United States Patent [19]

Berg

[11] Patent Number: 5,382,330
[45] Date of Patent: Jan. 17, 1995

[54] SEPARATION OF 1-OCTENE FROM OCTANE BY AZEOTROPIC DISTILLATION

[75] Inventor: Lloyd Berg, 1314 S. Third Ave., Bozeman, Mont. 59715

[73] Assignee: Lloyd Berg

[21] Appl. No.: 209,252

[22] Filed: Mar. 14, 1994

[51] Int. Cl.$^6$ ............................ B01D 3/36; C07C 7/06
[52] U.S. Cl. ............................ 203/60; 203/63; 585/862; 585/866
[58] Field of Search ............ 203/63, 60, 62, 56, 203/51; 585/866, 862

[56] References Cited

U.S. PATENT DOCUMENTS

| | | | |
|---|---|---|---|
| 2,186,524 | 1/1940 | Frey et al. | 203/60 |
| 2,461,993 | 2/1949 | McKinnis | 203/62 |
| 3,087,866 | 4/1963 | Burch | 203/60 |
| 5,100,515 | 3/1992 | Lee et al. | 203/63 |

Primary Examiner—Wilbur Bascomb, Jr.

[57] ABSTRACT

1-Octene is difficult to separate from octane by conventional distillation or rectification because of the proximity of their boiling points. 1-Octene can be readily separated from octane by azeotropic distillation. Effective agents are ethyl formate, ethyl acetate and t-amyl methyl ether.

2 Claims, No Drawings

SEPARATION OF 1-OCTENE FROM OCTANE BY AZEOTROPIC DISTILLATION

FIELD OF THE INVENTION

This invention relates to a method for separating 1-octene from octane using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

In the Fischer-Tropsch process for converting carbon monoxide and hydrogen into liquids, gases and waxes, hundreds of different hydrocarbons and oxygenated compounds are formed, most of them in very small amounts. One valuable compound occuring in reasonable quantities is 1-octene, b.p.=123° C. When this compound is separated by precision fractionation, all but the closest boiling compounds are separated. The closest is octane, b.p.=126° C. Azeotropic distillation would be an attractive method of effecting the separation of 1-octene from octane if agents can be found that will (1) create a large apparent relative volatility between 1-octene and octane and (2) are easy to recover from 1-octene. 1-Octene and octane boil three degrees apart and thus are impractical to separate by conventional rectification. Table 1 shows the relative volatility required to get 99% purity. With no agent, the relative volatility is 1.2 and 68 actual plates are required. With an agent giving a relative volatility of 1.9, only twenty plates are required.

TABLE 1

Theoretical and Actual Plates Required vs. Relative Volatility for 1-Octene - Octane Separation

| Relative Volatility | Theoretical Plates Required At Total Reflux, 99% Purity | Actual Plates Required, 75% Efficiency |
| --- | --- | --- |
| 1.2 | 51 | 68 |
| 1.5 | 23 | 31 |
| 1.9 | 15 | 20 |

OBJECTIVE OF THE INVENTION

The object of this invention is to provide a process or method of azeotropic distillation that will enhance the relative volatility of 1-octene from octane in their separation in a rectification column. It is a further object of this invention to identify organic compounds which in addition to the above constraints, are stable, can be separated from 1-octene and recycled to the azeotrope column with little decomposition.

SUMMARY OF THE INVENTION

The objects of this invention are provided by a process for separating 1-octene from octane which entails the use of certain organic compound as the agent in azeotropic distillation.

DETAILED DESCRIPTION OF THE INVENTION

I have discovered that certain organic compounds will greatly improve the relative volatility of 1-octene to octane and permit the separation of 1-decene from decane by rectification when employed as the agent in extractive distillation. They are methyl acetate, ethyl acetate, ethyl formate, t-amyl methyl ether and dimethylacetamide.

TABLE 2

Effective Azeotropic Distillation Agents For separating 1-Octene From Octane

| Compounds | Relative Volatility |
| --- | --- |
| None | 1.2 |
| Methyl acetate | 1.5 |
| Ethyl acetate | 1.6 |
| Ethyl formate | 1.9 * |
| t-Amyl methyl ether | 1.8 * |
| Dimethylacetamide | 1.5 |

* Brings octane out as overhead product

THE USEFULNESS OF THE INVENTION

The usefulness or utility of this invention can be demonstrated by referring to the data presented in Tables 1 and 2. All of the successful agents show that 1-octene can be separated from octane by means of azeotropic distillation in a rectification column and that the ease of separation as measured by relative volatility is considerable.

WORKING EXAMPLES

Example 1

Twenty grams of octane, 80 grams of 1-octene and 50 grams of ethyl acetate were charged to a vapor-liquid equilibrium still and refluxed for twelve hours. Analysis indicates a vapor composition of 21.3% octane, 78.7% 1-octene; a liquid composition of 30.6% octane, 69.4% 1-octene. This is a relative volatility of 1.6.

Example 2

Sixty grams of 1-octene, 40 grams of octane and 150 grams of t-amyl methyl ether were placed in the stillpot of a 7.3 theoretical plate glass perforated plate rectification column and refluxed for four hours. The overhead composition was 99.2% octane, 0.8% 1-octene; the bottoms composition was 60.7% octane, 39.3% 1-octene which is a relative volatility of 1.82.

Example 3

Sixty grams of 1-octene, 40 grams of octane and 150 grams of ethyl formate were placed in the stillpot of a 7.3 theoretical plate glass perforated plate rectification and refluxed for four hours. The overhead composition was 97.9% octane, 2.1% 1-octene; the bottoms composition was 28.3% octane, 71.7% 1-octene which is a relative volatility of 1.93.

I claim:

1. A method for recovering 1-octene from a mixture of 1-octene and octane which comprises distilling a mixture of 1-octene and octane in the presence of an azeotrope forming agent, recovering the octane and the azeotrope forming agent as overhead product and obtaining the 1-octene as bottoms product, wherein said azeotrope forming agent consists of one material selected from the group consisting of ethyl formate and t-amyl methyl ether.

2. A method for recovering 1-octene from a mixture of 1-octene and octane which comprises distilling a mixture of 1-octene and octane in the presence of an azeotrope forming agent, recovering the 1-octene and the azeotrope forming agent as overhead product and obtaining the octane as bottoms product, wherein said azeotrope forming agent consists of one material selected from the group consisting of methyl acetate, ethyl acetate and dimethylacetamide.

* * * * *